(12) United States Patent
Cheng et al.

(10) Patent No.: US 6,506,953 B1
(45) Date of Patent: Jan. 14, 2003

(54) HYDROALKYLATION OF AROMATIC HYDROCARBONS

(75) Inventors: Jane Chi-Ya Cheng, Voorhees, NJ (US); Ajit B. Dandekar, Marlton, NJ (US); Michael Alan Steckel, Media, PA (US); Hye Kyung Cho Timken, Woodbury, NJ (US)

(73) Assignee: ExxonMobil Oil Corporation, Fairfax, VA (US)

( * ) Notice: Subject to any disclaimer, the term of this patent is extended or adjusted under 35 U.S.C. 154(b) by 0 days.

(21) Appl. No.: 09/490,433

(22) Filed: Jan. 24, 2000

(51) Int. Cl.⁷ ............................ C07C 5/10; C07C 15/12
(52) U.S. Cl. ................... 585/269; 585/270; 585/268; 585/427; 585/467
(58) Field of Search ................. 585/270, 269, 585/268, 427, 467

(56) References Cited

U.S. PATENT DOCUMENTS

| | | |
|---|---|---|
| 3,354,078 A | 11/1967 | Miale et al. |
| 4,094,918 A | 6/1978 | Murtha et al. ........... 260/668 R |
| 4,118,434 A | 10/1978 | Murtha et al. ........... 260/668 R |
| 4,122,125 A | 10/1978 | Murtha et al. ........... 260/668 R |
| 4,177,165 A | 12/1979 | Murtha et al. ........... 252/455 Z |
| 4,206,082 A | 6/1980 | Murtha et al. ........... 252/455 Z |
| 4,219,687 A | 8/1980 | Dolhyj et al. ................ 585/267 |
| 4,219,689 A | 8/1980 | Murtha ....................... 585/425 |
| 5,053,571 A | 10/1991 | Makkee ..................... 585/425 |
| 6,049,018 A | * 4/2000 | Calabro et al. ............. 585/446 |

FOREIGN PATENT DOCUMENTS

| | | |
|---|---|---|
| EP | 0 006 401 | 6/1978 |
| EP | 0 002 824 | 12/1978 |
| GB | 1184022 | 2/1969 |
| WO | 00/43316 | 7/2000 |

OTHER PUBLICATIONS

Journal of Catalysts 4, pp. 527–529 (1965), Superactive Crystalline Aluminosilicate Hydrocarbon Catalysts, P.B. Weisz and J.N. Maile.
Journal of Catalysts 6, pp. 278–287 (1966), Catalysts by Crystalline Aluminosilicates IV. Attainable Catalytic Cracking Rate Constants, and Superactivity, J.N. Miale, N.Y. Chen and P.B. Weisz.
Journal of Catalysts 61, pp. 390–396 (1980), Chemical and Physical Properties of the ZSM–5 Substitutional Series, D.H. Olsen, W.O. Haag and R.M. Lago.

* cited by examiner

*Primary Examiner*—Bekir L. Yildirim
(74) *Attorney, Agent, or Firm*—Darryl M. Tyus

(57) ABSTRACT

There is described a process the hydroalkylation of an aromatic hydrocarbon, particularly benzene, to produce a cycloalkyl-substituted aromatic compound, particularly cyclohexylbenzene, comprising the step of contacting the aromatic hydrocarbon with hydrogen in the presence of a catalyst comprising MCM-68 and at least one metal having hydrogenation activity.

10 Claims, 1 Drawing Sheet

HYDROALKYLATION OF AROMATIC HYDROCARBONS

FIELD OF INVENTION

This invention relates to a process for the hydroalkylation of aromatic compounds and particularly to a process for the hydroalkylation of benzene to produce cyclohexylbenzene.

BACKGROUND TO THE INVENTION

Cyclohexylbenzene can be used to produce phenol, which is one of the most important industrial chemicals in the world. As of December 1995, more than 88% of world phenol capacity was based on cumene peroxidation with acetone coproduction. One of the primary economic difficulties of the cumene peroxidation route is that it requires the existence of an available market for the co-produced acetone. Currently, the growth of market demand for phenol exceeds that for acetone, and hence there exists an acetone oversupply problem. It is expected that this unbalanced growth will continue for some time.

Hydroperoxidation of cyclohexylbenzene (analogous to cumene peroxidation) could offer an alternative route for phenol production without the problem of acetone co-production. This alternative route co-produces cyclohexanone, which is a much more valuable and desirable by-product than acetone. Thus cyclohexanone is useful for the manufacture of caprolactam and nylon.

Dehydrogenation of cyclohexylbenzene also offers a low cost alternative to produce diphenyl from benzene. Diphenyl is used mainly for heat-transfer applications. Currently the main source of diphenyl is as a by-product (1 g diphenyl/100 g benzene) in benzene production by toluene dealkylation. The crude diphenyl is refined to 93–97% purity by distillation. High purity diphenyl can also be produced by direct thermal dehydrocondensation of benzene at 700–800° C. in gas or electrically heated tubular reactors. This process is energy intensive and produces by-products of terphenyl, higher polyphenyls and tars.

It is known that cyclohexylbenzene can be produced from benzene by the process of hydroalkylation or reductive alkylation. In this process, benzene is heated with hydrogen in the presence of a catalyst such that the benzene undergoes partial hydrogenation to produce cyclohexene which then alkylates the benzene starting material. Thus U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. More recently, U.S. Pat. No. 5,053,571 has proposed the use of ruthenium and nickel supported on zeolite beta as an aromatic hydroalkylation catalyst.

It has now been found that the recently discovered zeolite designated MCM-68, when combined with a hydrogenation metal, has activity for the hydroalkylation of aromatic hydrocarbons to produce cycloalkyl-substituted aromatic compounds, such as cyclohexylbenzene.

SUMMARY OF THE INVENTION

According to one aspect of the invention there is provided a process for the hydroalkylation of an aromatic hydrocarbon comprising the step of contacting the aromatic hydrocarbon with hydrogen in the presence of a catalyst comprising a first metal having hydrogenation activity and a porous crystalline material, MCM-68, which contains at least one channel system, in which each channel is defined by a 12-membered ring of tetrahedrally coordinated atoms, and at least two further, independent channel systems, in each of which each channel is defined by a 10-membered ring of tetrahedrally coordinated atoms, wherein the number of unique 10-membered ring channels is twice the number of 12-membered ring channels.

Preferably, the aromatic hydrocarbon is benzene.

Preferably, the first metal is selected from palladium, ruthenium, nickel and cobalt.

Preferably, the catalyst also contains a second metal, different from the first metal, and selected from zinc, tin, nickel and cobalt.

DETAILED DESCRIPTION OF THE INVENTION

The hydroalkylation process of the invention employs the synthetic porous crystalline material MCM-68, which is a single crystalline phase which has a unique 3-dimensional channel system comprising at least one channel system, in which each channel is defined by a 12-membered ring of tetrahedrally coordinated atoms, and at least two further independent channel systems, in which each channel is defined by a 10-membered ring of tetrahedrally coordinated atoms, wherein the number of unique 10-membered ring channels is twice the number of 12-membered ring channels. The normal crystalline form of MCM-68 contains one 12-membered ring channel system and two 10-membered ring channel systems, in which the channels of each system extend perpendicular to the channels of the other systems and in which the 12-ring channels are generally straight and the 10-ring channels are tortuous (sinusoidal).

Figure 1:
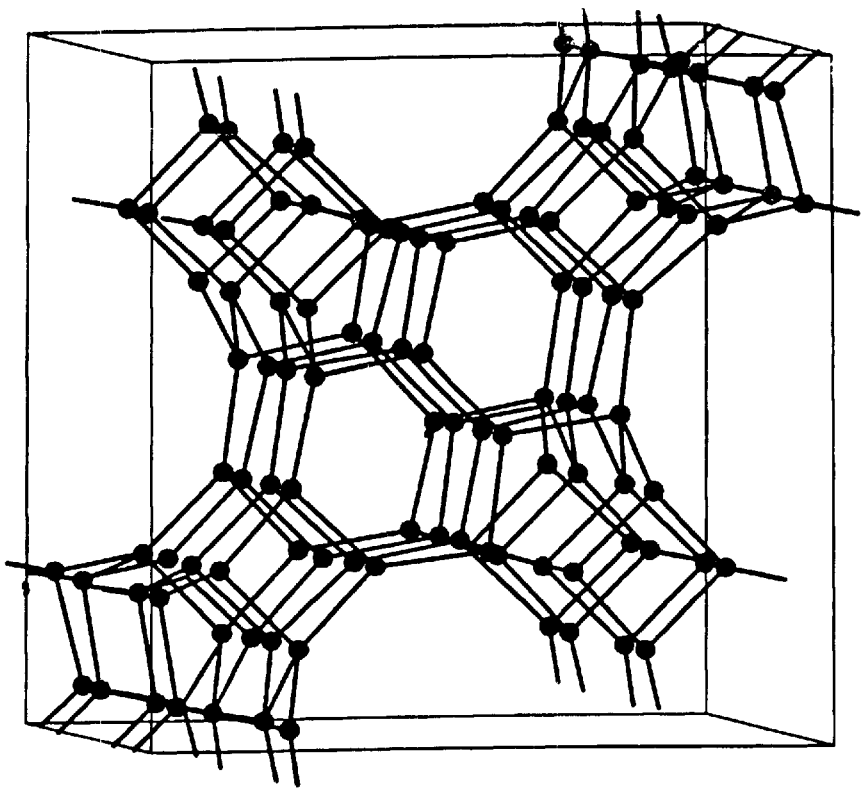
FIG. 1 is a schematic, three-dimensional illustration of a unit cell of MCM-68, showing only the tetrahedral atoms and the linkage between the tetrahedral atoms.
Figure 2:
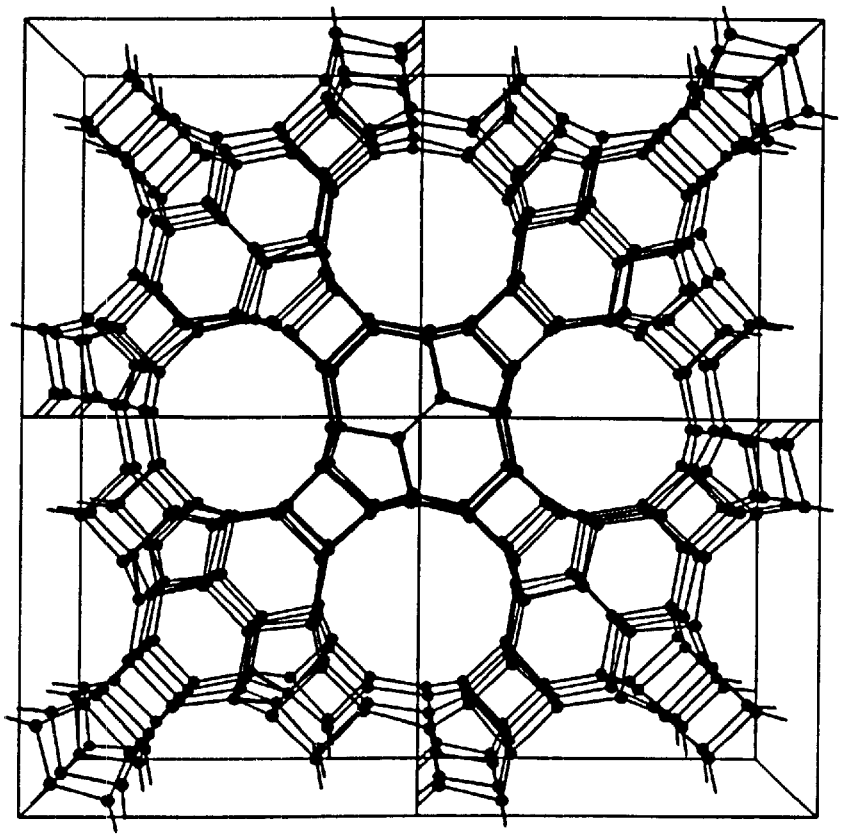
FIG. 2 is a schematic, three-dimensional illustration similar to FIG. 1 but of a plurality of unit cells.

The structure of MCM-68 may be defined by its unit cell, which is the smallest structural unit containing all the structural elements of the material. Table 1 lists the positions of each tetrahedral atom in the unit cell in nanometers; each tetrahedral atom is bonded to an oxygen atom which is also bonded to an adjacent tetrahedral atom. The structure represented by Table 1 is shown in FIG. 1 (which shows only the tetrahedral atoms). More extended versions of the structure are simply generated by attaching identical unit cells in any of the x, y or z directions. A more extended structure, illustrating the pores, is shown in FIG. 2. Since the tetrahedral atoms may move about due to other crystal forces (presence of inorganic or organic species, for example), a range of ±0.05 nm is implied for each coordinate position.

TABLE 1

|   |   | x | y | z |
|---|---|---|---|---|
| T | 1 | 0.242 | 1.370 | 0.242 |
| T | 2 | 0.241 | 1.372 | 0.552 |
| T | 3 | 0.051 | 0.400 | 0.152 |
| T | 4 | 0.244 | 0.463 | 0.383 |

TABLE 1-continued

|   | | x | y | z |
|---|---|---|---|---|
| T | 5 | 0.056 | 0.406 | 0.623 |
| T | 6 | 0.110 | 0.110 | 0.244 |
| T | 7 | 0.110 | 0.110 | 0.554 |
| T | 8 | 0.247 | 0.464 | 0.856 |
| T | 9 | 1.587 | 0.459 | 0.242 |
| T | 10 | 1.588 | 0.457 | 0.552 |
| T | 11 | 1.778 | 1.429 | 0.152 |
| T | 12 | 1.585 | 1.366 | 0.383 |
| T | 13 | 1.772 | 1.422 | 0.623 |
| T | 14 | 1.718 | 1.718 | 0.244 |
| T | 15 | 1.718 | 1.718 | 0.554 |
| T | 16 | 1.582 | 1.365 | 0.856 |
| T | 17 | 1.373 | 1.156 | 1.250 |
| T | 18 | 1.372 | 1.156 | 1.561 |
| T | 19 | 0.515 | 0.965 | 1.161 |
| T | 20 | 0.451 | 1.158 | 1.391 |
| T | 21 | 0.508 | 0.971 | 1.632 |
| T | 22 | 0.804 | 1.025 | 1.253 |
| T | 23 | 0.804 | 1.025 | 1.563 |
| T | 24 | 0.451 | 1.161 | 1.865 |
| T | 25 | 0.455 | 0.672 | 1.250 |
| T | 26 | 0.457 | 0.673 | 1.561 |
| T | 27 | 1.314 | 0.864 | 1.161 |
| T | 28 | 1.377 | 0.671 | 1.391 |
| T | 29 | 1.321 | 0.858 | 1.632 |
| T | 30 | 1.025 | 0.804 | 1.253 |
| T | 31 | 1.025 | 0.804 | 1.563 |
| T | 32 | 1.378 | 0.668 | 1.865 |
| T | 33 | 0.672 | 0.455 | 0.767 |
| T | 34 | 0.673 | 0.457 | 0.456 |
| T | 35 | 0.864 | 1.314 | 0.856 |
| T | 36 | 0.671 | 1.377 | 0.626 |
| T | 37 | 0.858 | 1.321 | 0.385 |
| T | 38 | 0.804 | 1.025 | 0.764 |
| T | 39 | 0.804 | 1.025 | 0.455 |
| T | 40 | 0.668 | 1.378 | 0.153 |
| T | 41 | 1.156 | 1.373 | 0.767 |
| T | 42 | 1.156 | 1.372 | 0.456 |
| T | 43 | 0.965 | 0.515 | 0.856 |
| T | 44 | 1.158 | 0.451 | 0.626 |
| T | 45 | 0.971 | 0.508 | 0.385 |
| T | 46 | 1.025 | 0.804 | 0.764 |
| T | 47 | 1.025 | 0.804 | 0.455 |
| T | 48 | 1.161 | 0.451 | 0.153 |
| T | 49 | 1.370 | 0.242 | 1.775 |
| T | 50 | 1.372 | 0.241 | 1.465 |
| T | 51 | 0.400 | 0.051 | 1.865 |
| T | 52 | 0.463 | 0.244 | 1.635 |
| T | 53 | 0.406 | 0.056 | 1.394 |
| T | 54 | 0.110 | 0.110 | 1.773 |
| T | 55 | 0.110 | 0.110 | 1.463 |
| T | 56 | 0.464 | 0.247 | 1.161 |
| T | 57 | 0.459 | 1.587 | 1.775 |
| T | 58 | 0.457 | 1.588 | 1.465 |
| T | 59 | 1.429 | 1.778 | 1.865 |
| T | 60 | 1.366 | 1.585 | 1.635 |
| T | 61 | 1.422 | 1.772 | 1.394 |
| T | 62 | 1.718 | 1.718 | 1.773 |
| T | 63 | 1.718 | 1.718 | 1.463 |
| T | 64 | 1.365 | 1.582 | 1.161 |
| T | 65 | 1.587 | 0.459 | 1.775 |
| T | 66 | 1.588 | 0.457 | 1.465 |
| T | 67 | 1.778 | 1.429 | 1.865 |
| T | 68 | 1.585 | 1.366 | 1.635 |
| T | 69 | 1.772 | 1.422 | 1.394 |
| T | 70 | 1.582 | 1.365 | 1.161 |
| T | 71 | 0.242 | 1.370 | 1.775 |
| T | 72 | 0.241 | 1.372 | 1.465 |
| T | 73 | 0.051 | 0.400 | 1.865 |
| T | 74 | 0.244 | 0.463 | 1.635 |
| T | 75 | 0.056 | 0.406 | 1.394 |
| T | 76 | 0.247 | 0.464 | 1.161 |
| T | 77 | 0.455 | 0.672 | 0.767 |
| T | 78 | 0.457 | 0.673 | 0.456 |
| T | 79 | 1.314 | 0.864 | 0.856 |
| T | 80 | 1.377 | 0.671 | 0.626 |
| T | 81 | 1.321 | 0.858 | 0.385 |
| T | 82 | 1.378 | 0.668 | 0.153 |
| T | 83 | 1.373 | 1.156 | 0.767 |
| T | 84 | 1.372 | 1.156 | 0.456 |
| T | 85 | 0.515 | 0.965 | 0.856 |
| T | 86 | 0.451 | 1.158 | 0.626 |
| T | 87 | 0.508 | 0.971 | 0.385 |
| T | 88 | 0.451 | 1.161 | 0.153 |
| T | 89 | 1.156 | 1.373 | 1.250 |
| T | 90 | 1.156 | 1.372 | 1.561 |
| T | 91 | 0.965 | 0.515 | 1.161 |
| T | 92 | 1.158 | 0.451 | 1.391 |
| T | 93 | 0.971 | 0.508 | 1.632 |
| T | 94 | 1.161 | 0.451 | 1.865 |
| T | 95 | 0.672 | 0.455 | 1.250 |
| T | 96 | 0.673 | 0.457 | 1.561 |
| T | 97 | 0.864 | 1.314 | 1.161 |
| T | 98 | 0.671 | 1.377 | 1.391 |
| T | 99 | 0.858 | 1.321 | 1.632 |
| T | 100 | 0.668 | 1.378 | 1.865 |
| T | 101 | 0.459 | 1.587 | 0.242 |
| T | 102 | 0.457 | 1.588 | 0.552 |
| T | 103 | 1.429 | 1.778 | 0.152 |
| T | 104 | 1.366 | 1.585 | 0.383 |
| T | 105 | 1.422 | 1.772 | 0.623 |
| T | 106 | 1.365 | 1.582 | 0.856 |
| T | 107 | 1.370 | 0.242 | 0.242 |
| T | 108 | 1.372 | 0.241 | 0.552 |
| T | 109 | 0.400 | 0.051 | 0.152 |
| T | 110 | 0.463 | 0.244 | 0.383 |
| T | 111 | 0.406 | 0.056 | 0.623 |
| T | 112 | 0.464 | 0.247 | 0.856 |

MCM-68 can be prepared in essentially pure form with little or no detectable impurity crystal phases and, in its calcined form, has an X-ray diffraction pattern which is distinguished from the patterns of other known as-synthesized or thermally treated crystalline materials by the lines listed in Table 2 below. In its as-synthesized form, the crystalline MCM-68 material of the invention has an X-ray diffraction pattern which is distinguished from the patterns of other known as-synthesized or thermally treated crystalline materials by the lines listed in Table 3 below.

TABLE 2

| d(Å) | Relative Intensity [100 × I/I(o)] |
|---|---|
| 13.60 +/− 0.39 | S |
| 13.00 +/− 0.37 | VS |
| 10.92 +/− 0.31 | M |
| 10.10 +/− 0.29 | M |
| 9.18 +/− 0.26 | VS |
| 8.21 +/− 0.23 | W |
| 4.58 +/− 0.13 | W |
| 4.54 +/− 0.13 | W |
| 4.45 +/− 0.13 | VW-W |
| 4.32 +/− 0.12 | VW |
| 4.22 +/− 0.12 | VW |
| 4.10 +/− 0.12 | VS |
| 4.05 +/− 0.11 | M |
| 3.94 +/− 0.11 | M |
| 3.85 +/− 0.11 | M |
| 3.80 +/− 0.11 | VW |
| 3.40 +/− 0.10 | W |
| 3.24 +/− 0.09 | W |
| 2.90 +/− 0.08 | VW |

TABLE 3

| d(Å) | Relative Intensity [100 × I/I(o)] |
| --- | --- |
| 13.56 +/− 0.39 | VW |
| 12.93 +/− 0.37 | M-S |
| 10.92 +/− 0.31 | W |
| 10.16 +/− 0.29 | VW-W |
| 9.15 +/− 0.26 | VW-W |
| 8.19 +/− 0.23 | VW |
| 4.58 +/− 0.13 | W |
| 4.54 +/− 0.13 | W |
| 4.44 +/− 0.12 | W |
| 4.32 +/− 0.12 | VW |
| 4.23 +/− 0.12 | VW |
| 4.10 +/− 0.12 | VS |
| 4.06 +/− 0.12 | M |
| 3.98 +/− 0.11 | W |
| 3.88 +/− 0.11 | M |
| 3.80 +/− 0.11 | VW |
| 3.40 +/− 0.10 | VW |
| 3.24 +/− 0.09 | W |
| 2.90 +/− 0.08 | VW |

These X-ray diffraction data were collected with a Scintag diffraction system, equipped th a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units, and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (80–100), s=strong (60–80), m=medium (40–60), w=weak (20–40), and vw=very weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

MCM-68 has a composition involving the molar relationship:

$$X_2O_3:(n)YO_2,$$

wherein X is a trivalent element, such as aluminum, boron, iron, indium, and/or gallium, preferably aluminum; Y is a tetravalent element such as silicon, tin, titanium and/or germanium, preferably silicon; and n is at least about 5, such as 5 to 100,000, and usually from about 8 to about 50. In the as-synthesized form, the material has a formula, on an anhydrous basis and in terms of moles of oxides per n moles of $YO_2$, as follows:

$$(0.1-2)M_2O:(0.2-2)Q:X_2O_3:(n)YO_2$$

wherein M is an alkali or alkaline earth metal, and Q is an organic moiety. The M and Q components are associated with the material as a result of their presence during crystallization, and are easily removed by post-crystallization methods hereinafter more particularly described.

MCM-68 can be prepared from a reaction mixture containing sources of alkali or alkaline earth metal (M), e.g., sodium and/or potassium, cation, an oxide of trivalent element X, e.g., aluminum and/or boron, an oxide of tetravalent element Y, e.g., silicon, directing agent (Q), and water, said reaction mixture having a composition, in terms of mole ratios of oxides, within the following ranges:

| Reactants | Useful | Preferred |
| --- | --- | --- |
| $YO_2/X_2O_3$ | at least 5 | 8–50 |
| $H_2O/YO_2$ | 10–1000 | 15–100 |
| $OH/YO_2$ | 0.05–2 | 0.1–0.5 |
| $M/YO_2$ | 0.05–2 | 0.1–0.5 |
| $Q/YO_2$ | 0.01–1 | 0.05–0.2 |

The organic directing agent Q used herein is selected from the novel dications N,N,N', N'-tetraalkylbicyclo[2.2.2]oct-7-ene-2,3:5,6-dipyrrolidinium dication and N N,N',N'-tetraalkylbicyclo[2.2.2]octane-2,3:5,6-dipyrrolidinium dication which can be represented by the following formulae:

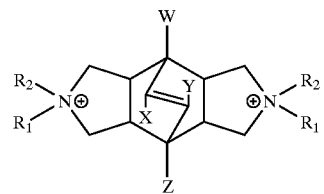

N,N,N',N'-tetraalkylbicyclo[2.2.2]oct-7-ene-2,3:5,6-dipyrrolidinium

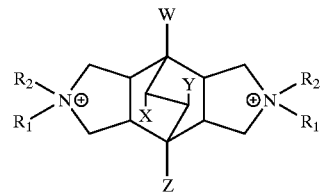

N,N,N',N'-tetraalkylbicyclo[2.2.2]octane-2,3:5,6-dipyrrolidinium where $R_1$, $R_2$ may be the same or different substituents selected from alkyl groups having 1 to 6 carbon atoms, phenyl and benzyl groups, or $R_1$ and $R_2$ may be linked as a cyclic group having 3 to 6 carbon atoms; and W, X, Y, Z may be the same or different substituents selected from hydrogen, alkyl groups having 1 to 6 carbon atoms, phenyl groups and halogens. In a preferred example, the organic directing agent is the N,N,N',N'-tetraethyl-exo,exo-bicyclo[2.2.2]oct-7-ene-2,3:5,6-dipyrrolidinium (Bicyclodiquat-$Et_4$) dication, having the formula $C_{20}H_{36}N_2^{++}$, which may be represented as follows:

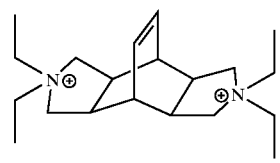

The source of the organic dication may be any salt which is not detrimental to the formation of the crystalline material of the invention, for example, the halide, e.g., iodide, or hydroxide salt.

The novel organic dications used to synthesize the MCM-68 of the invention can be prepared from, for example, exo,exo-bicyclo[2.2.2]oct-7-ene-2,3:5,6-tetracarboxylic dianhydride, which is a commercially available material. The dianhydride is initially reacted with ammonia or an amine to produce a diimide which is then reduced with $LiAlH_4$ to produce the diamine. The diamine can then be alkylated with an alkyl, phenyl or benzyl halide to produce the quaternary dication. Similarly, the bicyclooctane diquat can be produced from the dianhydride, which is known in the literature, or can be prepared by hydrogenation of the bicyclooctene dianhydride.

Crystallization of MCM-68 can be carried out at either static or stirred conditions in a suitable reactor vessel, such as for example, polypropylene jars or teflon lined or stainless steel autoclaves, at a temperature of 80° C. to about 250° C. for a time sufficient for crystallization to occur at the temperature used, e.g., from about 12 hours to about 100 days. Thereafter, the crystals are separated from the liquid and recovered.

It should be realized that the reaction mixture components can be supplied by more than one source. The reaction mixture can be prepared either batchwise or continuously. Crystal size and crystallization time will vary with the nature of the reaction mixture employed and the crystallization conditions.

Synthesis of MCM-68 may be facilitated by the presence of at least 0.01 percent, preferably 0.10 percent and still more preferably 1 percent, seed crystals (based on total weight) of crystalline product.

Prior to its use in the process of the invention, the as-synthesized MCM-68 is subjected to treatment to remove part or all of any organic constituent. This is conveniently achieved performed by heating at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product may then be converted into its active, hydrogen form, typically by the conventional steps of repeated ammonium exchange followed by calcination.

In its hydrogen form MCM-68 typically exhibits a high acid activity, with an alpha value of 900–1000. Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec-1). The Alpha Test is described in U.S. Pat. No. 3,354,078; in the *Journal of Catalysis*, 4, 527 (1965); 6, 278 (1966);. and 61, 395 (1980), each incorporated herein by reference as to that description. The experimental conditions of the test used herein include a constant temperature of 538° C. and a variable flow rate as described in detail in the Journal of Catalysis, 61, 395 (1980).

Prior to use in the process of the invention, it may be desirable to treat the MCM-68 to reduce its alpha activity to below 900 and more preferably to below 600. This is conveniently achieved by heating the crystalline material in the presence of steam at a temperature of 300 to 400° C. for 1 to 10 hours.

The catalyst employed in the process of the invention includes at least one hydrogenation metal in intimate combination with the MCM-68. The hydrogenation metal is preferably selected from palladium, ruthenium, nickel, cobalt and mixtures thereof, with palladium and ruthenium being particularly preferred. In addition, the catalyst may contain a further hydrogenation metal, such as platinum, rhodium and rhenium, in addition to said preferred hydrogenation metals. The amount of hydrogenation metal present in the catalyst may vary significantly and will, for example, depend on the particular metal employed. Preferably, however, the amount of hydrogenation metal present is between 0.05 and 10 wt %, and more preferably between 0.1 and 5 wt %, of the catalyst.

The catalyst preferably contains a second metal component, in addition to and different from the hydrogenation metal, which acts to promote the hydrogenation function of the catalyst. Suitable second metal components are selected from zinc, tin, nickel, cobalt and mixtures thereof. Again, the amount of second metal component present in the catalyst may vary significantly but preferably is between 0.05 and 10 wt %, and more preferably between 0.1 and 5 wt %, of the catalyst.

The metal component(s) can be in the combined with the MCM-68 by cocrystallization, by exchange into the composition to the extent a Group IIIA element, e.g., aluminum, is in the structure, impregnated therein or by intimate physical admixtured therewith.

The catalyst of the invention may also include a matrix or binder which is composited with the inorganic oxide material. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the inorganic oxide material employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of inorganic oxide material and binder may vary widely with the inorganic oxide material content ranging from about 1 to about 90 percent by weight and more usually in the range of about 30 to about 80 percent by weight of the composite The reaction conditions used in the process of the invention typically include a temperature of about 50 to 350° C., a pressure of about 100 to 7000 kPa, a benzene to hydrogen molar ratio of about 0.01 to 100 and a WHSV of about 0.01 to 100. In particular, it is important to keep the temperature as low as possible to minimize the formation of byproducts such as methylcyclopentane and methylcyclopentylbenzene. For this reason, the temperature is preferably maintained at or below about 150° C. and more preferably at or below about 120° C.

The products of the process of the invention will invariably include some dicycloalkylphenyl compounds which, where the aromatic feed is benzene, will be dicyclohexylbenzene (referred to as $C_{18}$ products in the Examples). Such dialkylated products can readily be separated from the effluent stream and converted to additional monoalkylated product by transalkylation with the aromatic feed, either by recycling the dialkylated product to the hydroalkylation reactor or by feeding the dialkylated product to separate transalkylation reactor. In the latter case, the transalkylation will preferably be effected in the presence of a catalyst, such as $WO_x/ZrO_2$, MCM-22, TEA-mordenite or zeolite beta.

The invention will now be more particularly described with reference to the accompanying Examples.

EXAMPLE 1

Synthesis of N,N'-Diethyl-exo,exo-bicyclo[2.2.2]oct-7-ene-2,3:5,6-tetracarboxylic diimide To a 2000-ml 3-necked round-bottomed flask equipped with a magnetic stirring bar, a reflux condenser and a thermometer were attached. The flask was then charged with 70 wt % ethylamine in water (515.25 g, 8 moles) followed by exo,exo-bicyclo[2.2.2]oct-7-ene-2,3:5,6-tetracarboxylic dianhydride (99.28 g, 0.4 moles) in portions along with vigorous stirring. After two hours of stirring at room temperature, water (300 ml) was added. The mixture was then stirred at 70° C. for 48 hours and then at 100° C. for 18 hours to drive off the excess amine. The reaction was then cooled to room temperature and the remaining ethylamine quenched with concentrated HCl in a dropwise fashion. The solid was then filtered under suction, washed with water (400 ml) and dried in a vacuum dessicator over drierite to give 120.90 g (100%) of diimide as white crystals.

Melting Point: 265–266° C.

NMR: Solvent=$CDCl_3$ $^{13}C$ ($\delta$/ppm): 12.846; 33.411; 33.776; 42.763; 130.685; 176.438.

$^1H$($\delta$/ppm): 1.07 (6H, t); 2.97 (4H, s); 3.47 (4H, q4); 3.78 (2H, br.s); 6.10

Combustion Analysis for $C_{16}H_{18}N_2O_4$

|  | % C | % H | % N |
| --- | --- | --- | --- |
| Calculated | 63.56 | 6.00 | 9.27 |
| Found | 63.45 | 6.00 | 9.21 |

EXAMPLE 2

Synthesis of N,N'-Diethyl-exo,exo-bicyclo[2.2.2]oct-7-ene-2,3:5,6-dipyrrolidine

All glassware in this procedure was dried in an oven at 150° C. for at least 12 hours. A 2000-ml, 3-necked round-bottomed flask equipped with a magnetic stirring bar, a thermometer and a graduated pressure equalized addition funnel sealed with a septum cap was comprehensively flushed with $N_2$. To this a soxhlet extractor with a thimble containing N,N'-diethyl-exo,exo-bicyclo[2.2.2]oct-7-ene-2,3:5,6-tetracarboxylic diimide (33.26 g,110 mmol) topped with a reflux condenser and an inline gas bubbler was attached. The system was then charged with lithium aluminum hydride powder (12.52 g, 330 mmol) and anhydrous THF (1650 ml) via the addition funnel. After 24 hours of reflux to fully extract and deliver the diimide, the reaction was cooled to 5° C. Then the reaction was quenched with water (12.5 ml), 15% NaOH solution (12.5 ml) and water (37.6 ml) keeping the temperature below 10° C. After warming to room temperature and suction filtration of the solids followed by washing with dichloromethane (660 ml), water (220 ml) was added to the combined filtrates which were then acidified using conc. HCl to pH=1–2. The organic layer was then separated, water (220 ml) added and the pH adjusted to 1–2 with concentrated HCl. This aqueous layer was separated and combined with the previous aqueous fraction, rendered basic with 50% NaOH solution to pH=11–12 and extracted with dichloromethane (5×275 ml). These combined organic fractions were dried over $Na_2SO_4$, filtered and evaporated in vacuum to give a yellow/orange oil which may solidify upon cooling (22.56 g, 83%). The oil was extracted with ether (2×150 mL), the fractions being filtered, combined, dried over $Na_2SO_4$, re-filtered & the solvent evaporated under vacuum to give a gold oil which solidifies upon cooling (20.15 g, 74%). $^1H$ and $^{13}C$ NMR analysis of the crude yellow solid showed no visible impurities and the diamine was used in this form in the subsequent diiodide preparation. However, an analytical sample of the diamine was obtained by vacuum distillation of the yellow solid (10 mTorr, 106–110° C.) to give a clear oil (52% efficiency) which crystallizes to a white solid on cooling.

Melting Point: 57–58° C.

NMR: Solvent=$CDCl_3$ $^{13}C$ ($\delta$/ppm): 13.837; 35.491; 44.210; 49.831; 58.423; 135.294.

$^1H$ ($\delta$/ppm): 1.05 (6H, t); 1.85 (4H, t); 2.37 (4H, q4); 2.49 (6H, br.d); 3.04

| Combustion Analysis for $C_{16}H_{26}N_2$ | | | |
| --- | --- | --- | --- |
|  | % C | % H | % N |
| Calculated | 77.99 | 10.64 | 11.37 |
| Found | 77.82 | 10.59 | 11.31 |

EXAMPLE 3

Synthesis of N,N,N',N'-Tetraethyl-exo,exo-bicyclo[2.2.2]oct-7-ene-2,3:5,6-dipyrrolidinium diiodide (Bicyclodiquat-$Et_4$2I)

To a 1000-ml 3-necked round-bottomed flask equipped with a magnetic stirring bar, a reflux condenser, a thermometer and a pressure equalized addition funnel containing a solution of iodoethane (67.37 g, 432 mmol) in ethanol (216 ml) were attached. The flask was then charged with N,N'-diethyl-exo,exo-bicyclo[2.2.2]oct-7-ene-2,3:5,6-dipyrrolidine (35.48 g, 144 mmol) and ethanol (144 ml). After stirring until all the solids had dissolved the iodoethane solution was added slowly and the mixture refluxed overnight. After subsequent cooling to 10° C., the solids were suction filtered and washed with acetone (144 ml). The resultant off-white solid was then refluxed in acetone (500 ml) for 15 minutes, suction filtered and dried in a vacuum dessicator over drierite to give a tan solid, 70.78 g (88%).

Melting Point: >270° C. (decomposition)

NMR: Solvent=$D_2O$ $^{13}C$ ($\delta$/ppm): 10.115; 10.932; 35.721; 42.597; 55.604; 58.370; 67.030; 130.870.

$^1H$ ($\delta$/ppm): 1.28 (12H, t); 2.85 (8H, br.s); 2.92 (2H, br.s); 3.32 (8H, q6); 3.81 (4H, d); 6.45 (2H, t).

| Combustion Analysis for $C_{20}H_{36}N_2I_2$ | | | |
|---|---|---|---|
| | % C | % H | % N |
| Calculated | 43.02 | 6.50 | 5.02 |
| Found | 43.19 | 6.58 | 4.85 |

EXAMPLE 4
Synthesis of Aluminosilicate MCM-68

14 g of Colloidal Silica Sol (30 wt % of $SiO_2$: Aldrich Ludox SM-30), and 22.096 g of distilled water are mixed with 0.6056 g of $Al(OH)_3$ (Aluminum Hydroxide, solid). To this reaction mixture added 7.354 g of KOH (88.8% purity) (Potassium Hydroxide, 20 wt % solution) and then added 3.912 g of Bicyclodiqaut-$Et_4$ 2I$^-$ (N,N,N',N'-Tetraethyl-exo, exo-bicyclo[2.2.2]oct-7-ene-2,3:5,6-dipyrrolidinium diiodide, solid). The reaction can be represented by the following mole ratios:

| | |
|---|---|
| $Si/Al_2$ | 18 |
| $H_2O/Si$ | 30 |
| OH/Si | 0.375 |
| $K^+$/Si | 0.375 |
| Bicyclodiquat-$Et_4$2I/Si | 0.10 |

The combined mixture was added to an autoclave and heated to 160° C. for 300 hours unstirred. The product was then filtered and washed with water and dried overnight under an IR lamp. The solid is subsequently calcined in air at a temperature of 540° C. for 8 hours to yield the material designated as MCM-68.

EXAMPLE 5
Ammonium Exchange and Preparation of H-MCM-68

The calcined MCM-68 material from Example 4 was ion exchanged 4 four times with a 1M ammonium nitrate solution at 80° C. then filtered washed and dried under an IR lamp. Subsequently it was calcined at 540° C. in air for 8 hrs. The H-MCM-68 obtained had an alpha value of a 1000.

EXAMPLE 6
Synthesis of Aluminosilicate MCM-68

7 g of Colloidal Silica (30 wt %), $Al(OH)_3$ (Aluminum Hydroxide, solid), KOH (Potassium Hydroxide, 20 wt % solution), Bicyclodiqaut-$Et_4$ 2I (N,N,N',N'-Tetraethyl-exo, exo-bicyclo[2.2.2]oct-7-ene-2,3:5,6-dipyrrolidinium diiodide, solid) and distilled water were combined in the following mole ratios:

| | |
|---|---|
| $Si/Al_2$ | 30 |
| $H_2O/Si$ | 30 |
| OH/Si | 0.375 |
| $K^+$/Si | 0.375 |
| Bicyclodiquat-$Et_4$2I/Si | 0.10 |

The combined mixture was added to an autoclave and heated to 160° C. for 150 hours. The product was then filtered and washed with water and dried overnight under an IR lamp. The solid was subsequently calcined in air at a temperature of 540° C. for 8 hours to yield the MCM-68. The powder x-ray diffraction of the final product showed the presence of trace amounts of zeolite ZSM-12.

EXAMPLE 7
Synthesis of Aluminosilicate MCM-68

7 g of Colloidal Silica (30 wt %), $Al(OH)_3$ (Aluminum Hydroxide, solid), KOH (Potassium Hydroxide, 20 wt % solution), Bicyclodiqaut-$Et_4$ 2I (N,N,N',N'-Tetraethyl-exo, exo-bicyclo[2.2.2]oct-7-ene-2,3:5,6-dipyrrolidinium diiodide, solid) and distilled water were combined in the following mole ratios:

| | |
|---|---|
| $Si/Al_2$ | 15 |
| $H_2O/Si$ | 30 |
| OH/Si | 0.375 |
| $K^+$/Si | 0.375 |
| Bicyclodiquat-$Et_4$2I/Si | 0.10 |

The combined mixture was added to an autoclave and heated to 160° C. for 240 hours. The product was then filtered and washed with water and dried overnight under an IR lamp. The solid was subsequently calcined in air at a temperature of 540° C. for 8 hours to yield MCM-68. The powder x-ray diffraction of the final product indicated the presence of trace amounts of zeolite Beta.

EXAMPLE 8
Synthesis of Aluminosilicate MCM-68

14 g of Colloidal Silica (30 wt %), $Al(OH)_3$ (Aluminum Hydroxide, solid), KOH (Potassium Hydroxide, 20 wt % solution), Bicyclodiqaut-$Et_4$ 2I (N,N,N',N'-Tetraethyl-exo, exo-bicyclo[2.2.2]oct-7-ene-2,3:5,6-dipyrrolidinium diiodide, solid) and distilled water were combined in the following mole ratios:

| | |
|---|---|
| $Si/Al_2$ | 18 |
| $H_2O/Si$ | 30 |
| OH/Si | 0.375 |
| $K^+$/Si | 0.375 |
| Bicyclodiquat-$Et_4$2I/Si | 0.10 |

The combined mixture was added to an autoclave and heated to 170° C. for 200 hours at 200 rpm. The product was then filtered and washed with water and dried overnight under an IR lamp. The solid was subsequently calcined in air at a temperature of 540° C. for 8 hours to yield MCM-68.

EXAMPLE 9
Synthesis of Aluminosilicate MCM-68 with 2 wt. % Seeds of As-synthesized MCM-68.

7 g of Colloidal Silica (30 wt %), $Al(OH)_3$ (Aluminum Hydroxide, solid), KOH (Potassium Hydroxide, 20 wt % solution), Bicyclodiqaut-$Et_4$ 2I (N,N,N',N'-Tetraethyl-exo, exo-bicyclo[2.2.2]oct-7-ene-2,3:5,6-dipyrrolidinium diiodide, solid) and distilled water were combined in the following mole ratios:

| | |
|---|---|
| $Si/Al_2$ | 18 |
| $H_2O/Si$ | 30 |
| OH/Si | 0.375 |
| $K^+$/Si | 0.375 |
| Bicyclodiquat-$Et_4$2I/Si | 0.10 |

To this mixture were added 2 wt. % seed crystals of as-synthesized MCM-68 from Example 5. The combined mixture was added to an autoclave and heated to 160° C. for 200 hours. The product was then filtered and washed with water and dried overnight under an IR lamp. The solid was subsequently calcined in air at a temperature of 540° C. for 8 hours to yield the material designated as MCM-68.

EXAMPLE 10

Preparation of an Alumina-bound 0.3Ru/0.3%Sn/MCM-68 Catalyst

As-synthesized MCM-68 with a silica-to-alumina ratio of 18 from Example 4 was used for this catalyst preparation. A physical mixture of 65 parts MCM-68 and 35 parts pseudo-boehmite alumina was mulled to form a uniform mixture. All components were blended based on parts by weight on a 100% solids basis. Sufficient amount of deionized water was added to form an extrudable paste. The mixture was auger extruded to 1/16-inch cylindrical shape extrudates and dried at 120° C. overnight. The K-containing MCM-68 extrudates were then calcined to remove the organic template and then exchanged with $NH_4NO_3$ solution followed by calcination to make the H-form. The H-form MCM-68 catalyst was steam deactivated at 370° C. for 4 hours. The steamed MCM-68 catalyst had a hexane cracking activity of 550 alpha.

0.02 g of tributyl tin acetate was dissolved in 2.5 ml of decane, and the resulting solution was used to impregnate 2.5 g of steamed H-MCM-68 using an incipient wetness method. The impregnated catalyst was calcined at 540° C. in flowing air for 3 h to yield 0.3%Sn/MCM-68. 0.03 g of hexammine ruthenium chloride was then dissolved in 2.2 g of distilled water, and the resulting solution was used to impregnate 2.5 g of 0.3% Sn/MCM-68 using an incipient wetness method. The impregnated catalyst was dried at 120° C. for 12 hours in air followed by calcination at 360° C. in flowing air for 3 hours to yield a 0.3% Ru/0.3%Sn/MCM-68 catalyst.

EXAMPLE 11

Hydroalkylation of Benzene Using 0.3Ru/0.3%Sn/MCM-68 Catalyst

The catalyst prepared in Example 10 was used for benzene hydroalkylation. Two grams of this catalyst was charged to a fixed-bed micro-reactor. The catalyst was pretreated with 50 cc/min of flowing hydrogen for 2 hours at 300° C. and 1 atm. After cooling to 120° C. in flowing hydrogen, benzene was fed into the reactor through a syringe pump at 60 cc/hour for 1 hour while the reactor pressure was increased to 150 psig. Benzene rate was then reduced to 2 WHSV and hydrogen/benzene ratio was adjusted to 1:1. Liquid products were collected in a cold product trap and analyzed by GC off-line.

The GC analysis of a sample after 19 hours on stream showed 46.5% benzene conversion. The selectivity for phenylcyclohexane was 41.9% by weight. Byproducts include cyclohexane (54.4%), dicyclohexylbenzene (2.7%), and other $C_{12}$ and $C_{18}$ species (1.0%).

What is claimed is:

1. A process for the hydroalkylation of an aromatic hydrocarbon comprising the step of contacting the aromatic hydrocarbon with hydrogen in the presence of a catalyst comprising a first metal having hydrogenation activity and a porous crystalline material which contains at least one channel system, in which each channel is defined by a 12-membered ring of tetrahedrally coordinate d a toms, and at least two further, independent channel systems, in each of which each channel is defined by a 10-membered ring of tetrahedrally coordinated atoms, wherein the number of unique 10-membered ring channels is twice th e number of 12-membered ring channels.

2. The process of claim 1 wherein said porous crystalline material contains one 12-membered ring channel system and two 10-membered ring channel systems.

3. The process of claim 2 in which the channels in each 10-membered ring channel system of crystalline material extend in a direction generally perpendicular to the channels in the other 10-membered ring channel system and to the channels in the 12-membered ring channel system.

4. A process for the hydroalkylation of an aromatic hydrocarbon comprising contacting the feedstock with a catalyst composition comprising a synthetic porous crystalline material comprising a framework of tetrahedral atoms bridged by oxygen atoms, the tetrahedral atom framework being defined by a unit cell with atomic coordinates in nanometers shown in Table 1, wherein each coordinate position may vary within ±0.05 nanometer.

5. A process for the hydroalkylation of an aromatic hydrocarbon comprising the step of contacting the aromatic hydrocarbon with hydrogen in the presence of a catalyst comprising a first metal having hydrogenation activity and a porous crystalline material characterized by an X-ray diffraction pattern including values substantially as set forth in Table 2 of the specification and having a composition comprising the molar relationship $$X_2O_3:(n)YO_2,$$

wherein n is at least about 5, X is a trivalent element, and Y is a tetravalent element.

6. The process of claim 5 wherein X comprises aluminum and Y comprises silicon.

7. The process of claim 1 wherein the aromatic hydrocarbon is benzene.

8. The process of claim 1 wherein the first metal is selected from palladium, ruthenium, nickel and cobalt.

9. The process of claim 1 wherein the catalyst also contains a second metal, different from the first metal, and selected from zinc, tin, nickel and cobalt.

10. The process of claim 1 wherein the contacting step is conducted at a temperature of about 50 to 350° C., a pressure of about 100 to 7000 kPa, a benzene to hydrogen molar ratio of about 0.01 to 100 and a WHSV of about 0.01 to 100.

\* \* \* \* \*